(12) United States Patent
Choudhri

(10) Patent No.: US 12,290,444 B2
(45) Date of Patent: May 6, 2025

(54) INTERVERTEBRAL IMPLANTS HAVING POSITIONING GROOVES AND KITS AND METHODS OF USE THEREOF

(71) Applicant: Haroon Fiaz Choudhri, Alpine, NJ (US)

(72) Inventor: Haroon Fiaz Choudhri, Alpine, NJ (US)

(73) Assignee: Haroon Choudhri, Alpine, NJ (US)

( * ) Notice: Subject to any disclaimer, the term of this patent is extended or adjusted under 35 U.S.C. 154(b) by 0 days.

(21) Appl. No.: 18/230,337

(22) Filed: Aug. 4, 2023

(65) Prior Publication Data

US 2023/0372109 A1 Nov. 23, 2023

Related U.S. Application Data

(63) Continuation of application No. 17/462,117, filed on Aug. 31, 2021, now Pat. No. 11,759,324.

(51) Int. Cl.
*A61F 2/44* (2006.01)
*A61F 2/30* (2006.01)
*A61F 2/46* (2006.01)

(52) U.S. Cl.
CPC ...... *A61F 2/30771* (2013.01); *A61F 2/30749* (2013.01); *A61F 2/442* (2013.01); *A61F 2/4455* (2013.01); *A61F 2/4611* (2013.01); *A61F 2002/3008* (2013.01); *A61F 2002/30112* (2013.01); *A61F 2002/30331* (2013.01); *A61F 2002/30593* (2013.01); *A61F 2002/30828* (2013.01)

(58) Field of Classification Search
CPC ........ A61F 2/442; A61F 2/4455; A61F 2/447; A61F 2/4611
See application file for complete search history.

(56) References Cited

U.S. PATENT DOCUMENTS

| | | | | |
|---|---|---|---|---|
| 5,888,227 A * | 3/1999 | Cottle | ............... | A61F 2/4455 623/17.16 |
| 6,143,033 A * | 11/2000 | Paul | ............... | A61F 2/447 623/17.11 |
| 6,224,631 B1 * | 5/2001 | Kohrs | ............... | A61F 2/446 623/17.11 |
| 6,261,296 B1 * | 7/2001 | Aebi | ............... | A61B 17/025 606/205 |
| 6,520,993 B2 * | 2/2003 | James | ............... | A61F 2/4465 623/17.16 |
| 7,303,583 B1 * | 12/2007 | Schar | ............... | A61F 2/442 623/17.16 |
| 2002/0116009 A1 | 8/2002 | Fraser et al. | | |

(Continued)

*Primary Examiner* — Matthew J Lawson
(74) *Attorney, Agent, or Firm* — Perilla Knox & Hildebrandt LLP; Stephanie L. Davy-Jow

(57) ABSTRACT

Spinal implants, spinal implant systems, and methods for inserting spinal implants are provided. The implants can be implanted in an intervertebral space between adjacent superior and inferior vertebrae. The implant includes a superior implant surface having one or more superior positioning grooves configured to receive a corresponding superior positioning rail and an inferior implant surface having one or more inferior positioning grooves configured to receive a corresponding inferior positioning rail when the implant is implanted in the intervertebral space.

20 Claims, 12 Drawing Sheets

(56) References Cited

U.S. PATENT DOCUMENTS

| | | | |
|---|---|---|---|
| 2004/0122518 A1* | 6/2004 | Rhoda | A61F 2/4611 623/17.11 |
| 2005/0143822 A1* | 6/2005 | Paul | A61F 2/4455 623/17.11 |
| 2005/0216084 A1 | 9/2005 | Fleischmann et al. | |
| 2006/0235520 A1* | 10/2006 | Pannu | A61B 17/025 606/90 |
| 2008/0306598 A1 | 12/2008 | Hansen et al. | |
| 2009/0024161 A1* | 1/2009 | Bonutti | A61B 17/7058 606/213 |
| 2011/0082552 A1 | 4/2011 | Wistrom et al. | |
| 2012/0116513 A1* | 5/2012 | Carpenter | A61F 2/4611 623/17.16 |
| 2014/0100657 A1 | 4/2014 | McCormack et al. | |
| 2017/0079805 A1* | 3/2017 | Costabile | A61F 2/447 |

* cited by examiner

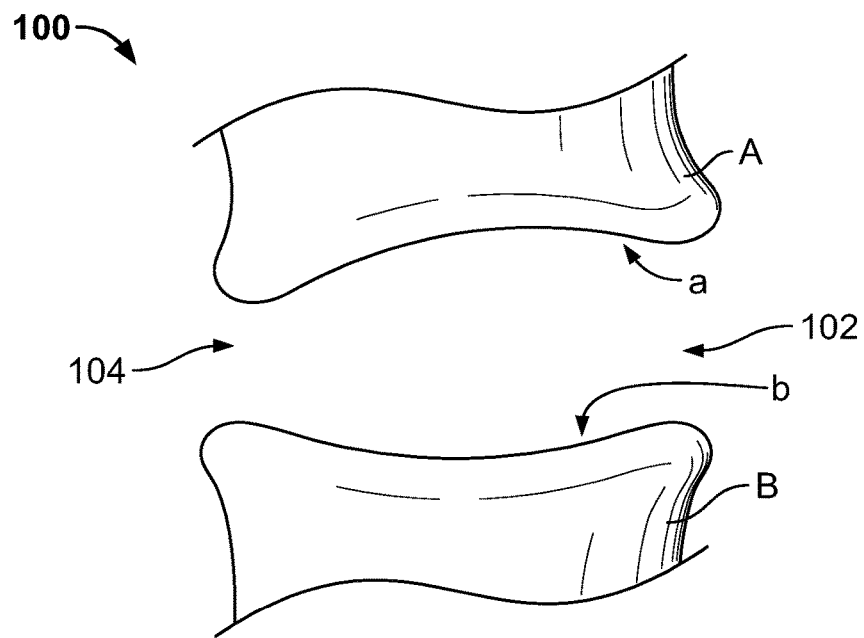
FIG. 1
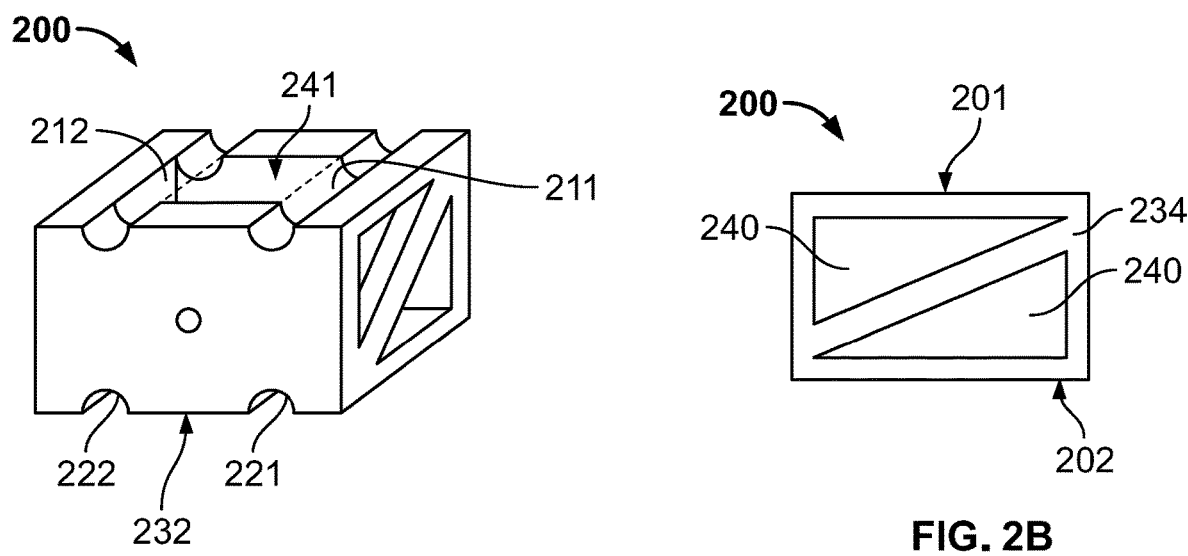
FIG. 2A
FIG. 2B

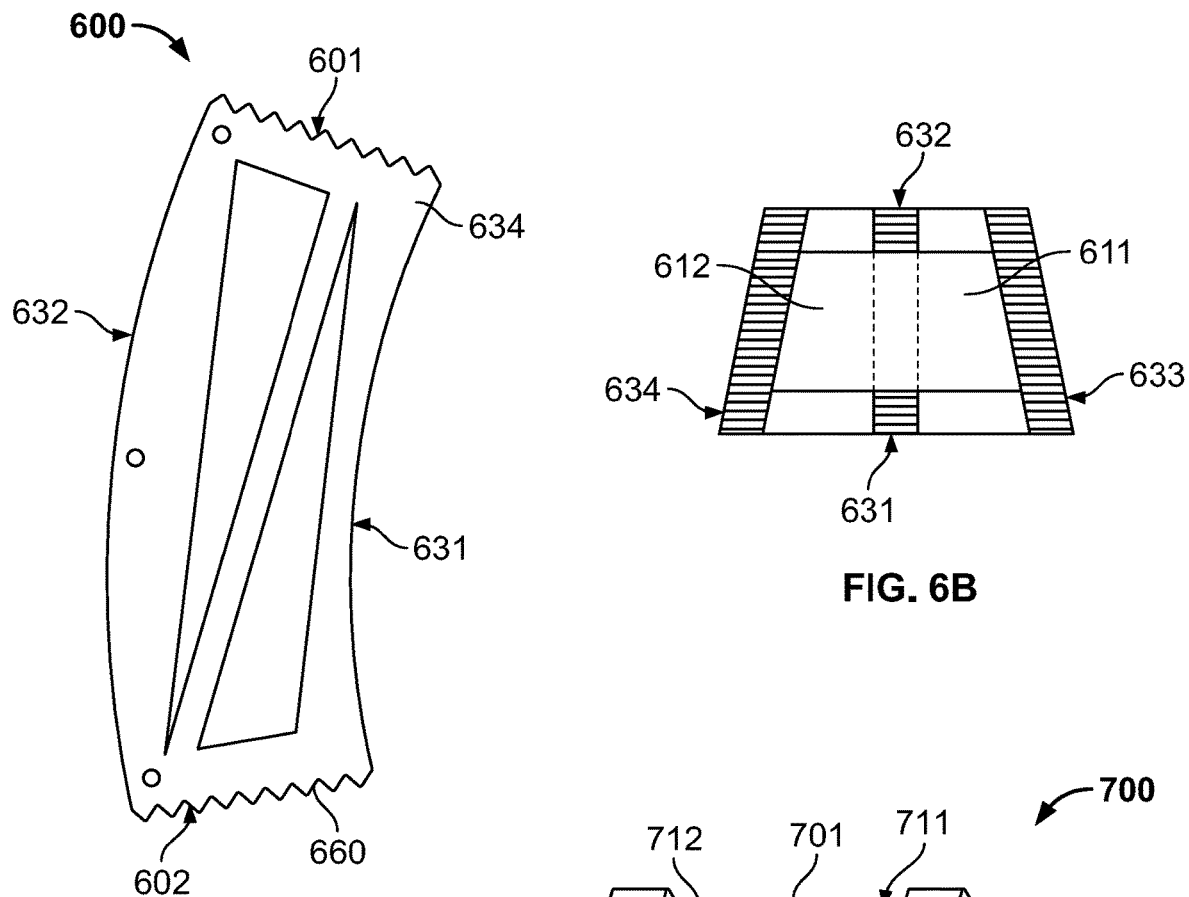
FIG. 6A
FIG. 6B
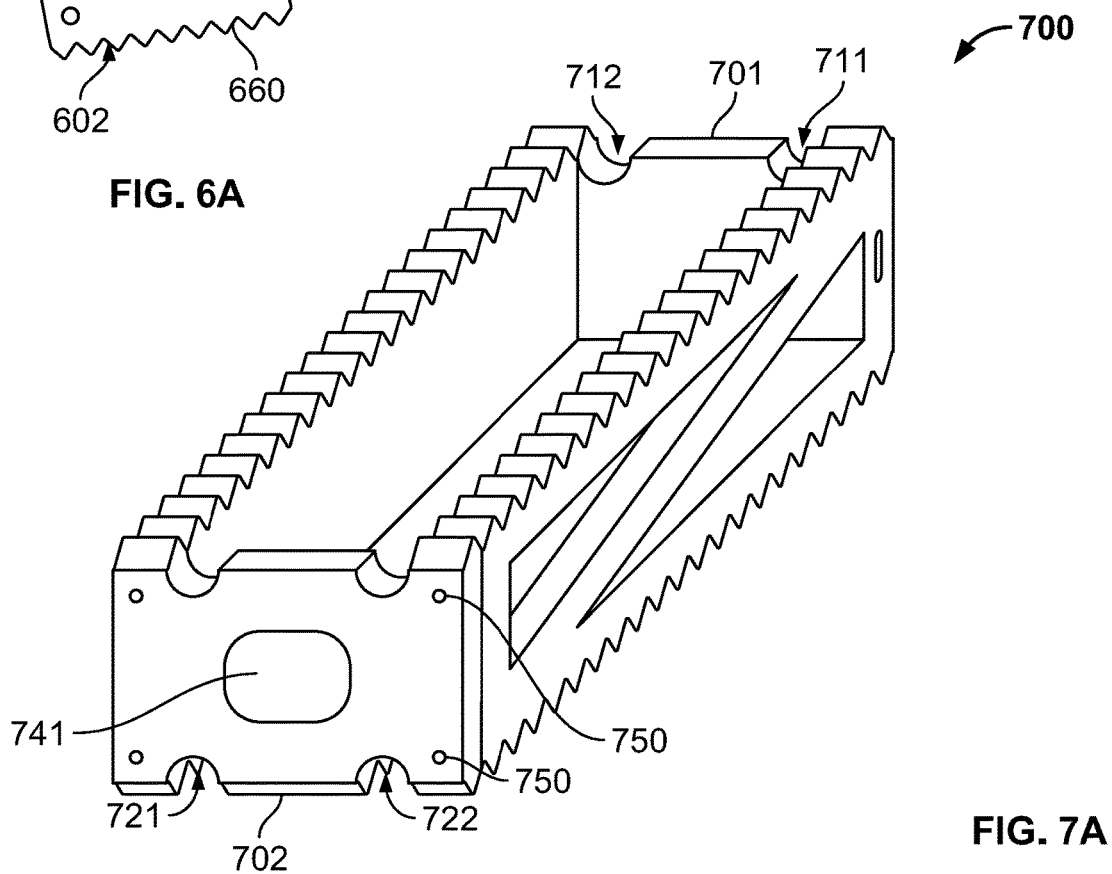
FIG. 7A

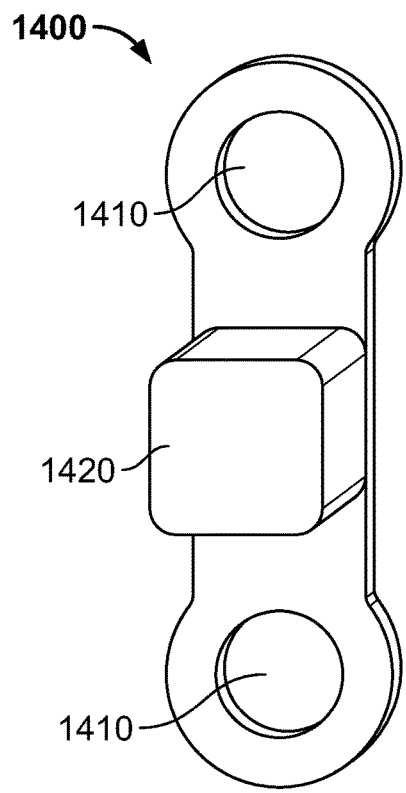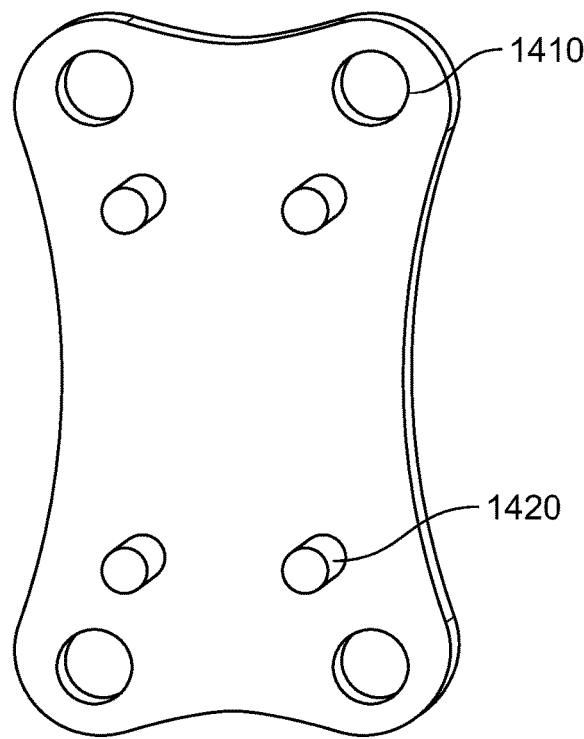
FIG. 14A
FIG. 14B
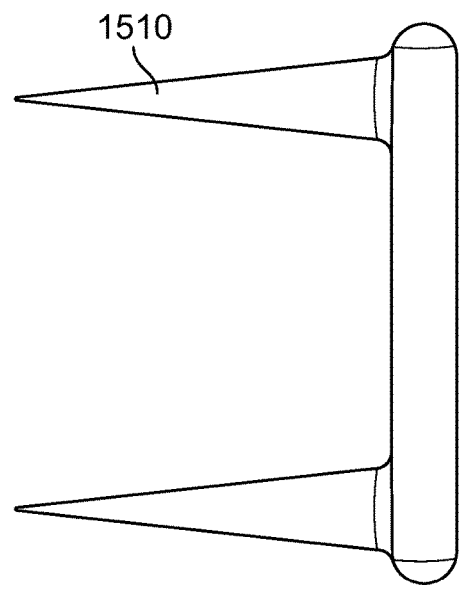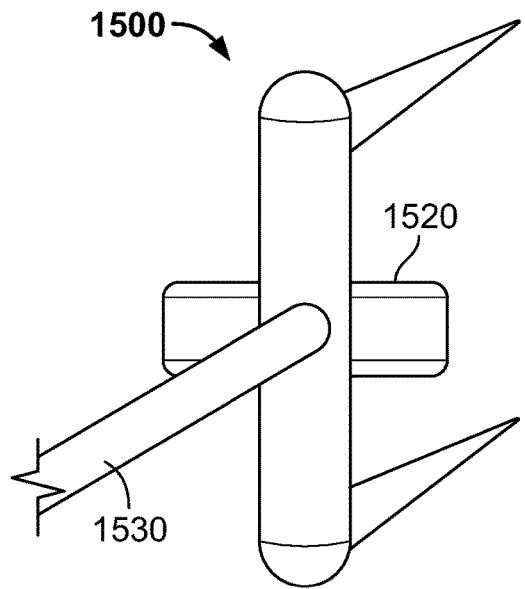
FIG. 15A
FIG. 15B

INTERVERTEBRAL IMPLANTS HAVING POSITIONING GROOVES AND KITS AND METHODS OF USE THEREOF

CROSS-REFERENCE TO RELATED APPLICATIONS

This application is a Continuation of application Ser. No. 17/462,117, having the title "INTERVERTEBRAL IMPLANTS HAVING POSITIONING GROOVES AND KITS AND METHODS OF USE THEREOF", filed on Aug. 31, 2021, the disclosure of which is incorporated herein by reference in its entirety.

TECHNICAL FIELD

The present disclosure generally relates to intervertebral implants and methods of use thereof.

BACKGROUND

The spinal disc and/or vertebral bodies can be displaced or damaged due to trauma, disease, degenerative defects, or wear over an extended period of time. One result of this displacement or damage to a spinal disc or vertebral body can be chronic back pain. Intervertebral disc degeneration impacts the majority of people, with more than 60% of patients beyond age 40 displaying some level of disc degeneration on an MRI. This is most prevalent in the lumbar spine.

The standard treatment for chronic pain related to damaged or displaced discs or segmental instability is lumbar spinal fusion. There are two main types of lumbar spinal fusion, which can be used in conjunction with each other. Posterolateral fusion places the bone graft between the transverse processes in the back of the spine. These vertebrae are then fixed in place with screws and/or wire through the pedicles of each vertebra attaching to a metal rod on each side of the vertebrae. Interbody fusion places the bone graft between the vertebra in the area usually occupied by the intervertebral disc. In preparation for the spinal fusion, the inner nucleus pulposus is removed entirely. A device such as an intervertebral cage or implant can be placed between the vertebra to restore proper spine alignment and disc height.

Cervical spinal fusions can be performed on the neck. Bone, metal plates, or screws can make a bridge between adjacent vertebrae. In advanced cases, whole vertebrae can be removed before the fusion occurs. Usually, however, only the intervertebral disk is removed, and a spacer—commonly made of metal, bone or PEEK—is subsequently inserted, allowing for the vertebrae to eventually heal together. Cervical spinal fusion can be performed for several reasons. Following injury, this surgery can help stabilize the neck and prevent fractures of the spinal column which could damage the spinal cord. It can also treat misaligned vertebrae or as a follow up for other spinal injuries. Cervical spinal fusion can remove or reduce pressure on nerve roots caused by bone fragments or ruptured intervertebral disks.

The success or failure of spinal fusion depends on several factors. For instance, the spacer or cage used to fill the space left by the removed disc and bony anatomy must be sufficiently strong to support the spine under a wide range of loading conditions. The implant should also be configured to remain in place once it has been positioned in the spine by the surgeon. Additionally, the bone graft materials used should be biocompatible and promote bony ingrowth. Facilitation of boney arthrodesis (fusion) is a desirable property of an interbody implant.

Common causes of failure in spinal fusion include slippage of the implant, breakage of the plates, or the backing out of screws that secure the implant. Screws back out, typically as a result of the failure of the screws to achieve a sufficient purchase in the bone; although the stripping of the threads on the screws also causes this problem. However, the hardware failures associated with the implant itself may include slippage, improper placement, or improper fit to the spinal geometry. There is a need for improved devices for spinal fusion and for improved, less invasive methods for achieving spinal fusion.

Therefore, it is an object of the disclosure to provide improved intervertebral implants that can be easily placed and with improved fit as compared to existing implants.

It is further an object of the disclosure to provide improved intervertebral fusion implants that remain in place following implantation.

It is further an object of the disclosure to provide improved and safer methods for spinal fusion, in particular for lumbar or cervical spinal fusion.

SUMMARY

Embodiments of the present disclosure provide for spinal implants and systems for surgical implants and placement thereof.

An embodiment of the present disclosure includes a spinal implant. The implant can include a superior implant surface having one or more superior positioning grooves configured to receive a corresponding superior positioning rail. The implant can also include an inferior implant surface having one or more inferior positioning grooves configured to receive a corresponding inferior positioning rail. One or more implant sidewalls can separate the superior implant surface and the inferior implant surface.

Another embodiment of the present disclosure includes a system for surgical implants. The system can include a positioning tool comprising at least one positioning rail and a spinal implant as above.

Other systems, methods, features, and advantages of the devices and methods will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 1 is a sectional dexter view onto the sagittal plane of an idealized intervertebral space. For clarity the intervertebral implant is not drawn.

FIGS. 2A-2C depict an exemplary anterior cervical discectomy and fusion (ACDF) implant. FIG. 2A is a perspective view of the exemplary cervical ACDF implant. FIG. 2B is a side view of the exemplary cervical ACDF implant. FIG. 2C is a top view of the exemplary cervical ACDF implant. Dashed lines are drawn to aid the viewer.

FIGS. 6A-6B depict an exemplary cervical corpectomy implant. FIG. 6A is a side view of the exemplary corpectomy implant. FIG. 6B is a top view of the exemplary corpectomy implant.

FIGS. 7A-7C depict an exemplary thoracolumbar implant designed for a lateral approach. FIG. 7A is a perspective view of the exemplary thoracolumbar implant. FIG. 7B is a side view of the exemplary thoracolumbar implant. FIG. 7C is a top view of the exemplary thoracolumbar implant.

FIG. 9A is a perspective view of the exemplary PLIF implant. FIG. 9B is a side view of the exemplary PLIF implant.

FIG. 11A is a perspective view of the exemplary TLIF implant. FIG. 11B is a top view of the exemplary TLIF implant.

FIG. 12A is a perspective view of the exemplary ALIF implant. FIG. 12B is a top view of the exemplary ALIF implant.

FIGS. 14A-14B are examples of stabilization (button) plates for retention and stabilization of the implants.

FIGS. 15A-15B depict exemplary affixing tools for placement of the button plates in FIGS. 14A-14B.

DETAILED DESCRIPTION

Figure 2C:
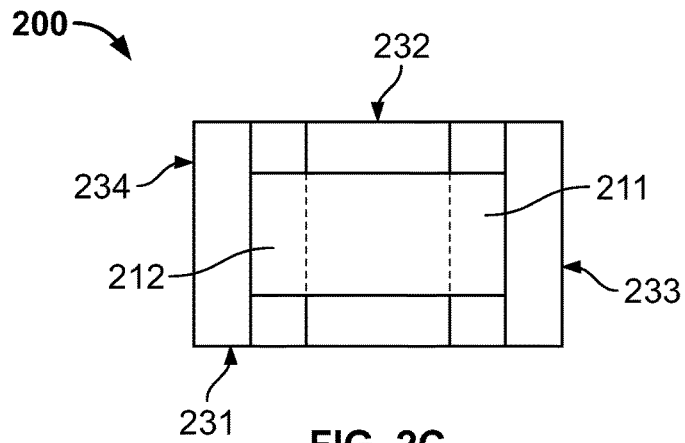

In various aspects, intervertebral implants for implantation in an intervertebral space between adjacent superior and inferior vertebrae are provided. The implants include a plurality of positioning grooves located on superior and inferior surfaces that can be slidably engaged by appropriately placed positioning rails on a device such as a detractor to allow for placement of the implant in the intervertebral space with greater ease and with greater retention in the intervertebral space.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein. These variants and adaptations are intended to be included in the teachings of this disclosure and to be encompassed by the claims herein.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant specification should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of neurosurgery and orthopedic surgery as well as medical device design and engineering and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'", where 'x' and 'y' are numerical values, includes "about 'x' to about 'y'".

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

Some basic terms and measures used to characterize the regions and dimension of the intervertebral space are depicted in FIG. 1. FIG. 1 is a dexter projection into the sagittal plane of the body of the intervertebral space 100 between an idealized superior (upper) vertebra A and an idealized inferior (lower) vertebra B. The reverse cage intervertebral implant and the intervertebral disc is removed in FIG. 1 for clarity. The intervertebral implants have a suitable shape and dimension so as to fit into the intervertebral space 100, engaging the superior vertebral surface a and the inferior vertebral surface b, and such that the spacer extends from the anterior region 102 of the intervertebral space 100 to the posterior region 104 of the intervertebral space 100.

Implants Having One or More Positioning Grooves

A variety of implants are provided for implantation in an intervertebral space between adjacent superior and inferior vertebrae. The implants can include one or more positioning grooves on the superior surface of the implant and one or more positioning grooves on the inferior surface of the implant to allow for ease of placement with improved fit and positioning. In particular, the one or more positioning grooves can be of a suitable size, shape, and orientation on the implant such that a positioning tool having one or more positioning rails can engage the positioning grooves.

In some embodiments, radiopaque markers may be incorporated into the implants to allow for radiographic localization of radiolucent implants.

A variety of positioning tools are also provided. The positioning tools include one or more positioning rails that correspond to one or more positioning grooves. For example, the positioning rails can be part of a vertebral distractor-inserter such that the rails insert in the positioning grooves. In certain embodiments, the positioning rails can be about 1 mm wide and about 1 mm to 1.5 mm high to engage with the positioning grooves on the implant. In certain embodiments, the positioning rails can have a length of about 10 to 12 mm in length for such as a cervical implant device. In other embodiments, the positioning rails can have a longer length for use in other devices (e.g. thoracic, lumbar, etc) of a different size. The positioning tools are described in further detail below.

Textured, Featured or Irregular Surface

Each surface of the intervertebral implant can partially or entirely include a featured and/or a textured or irregular surface. The features or texture on the surface(s) increase the frictional resistance between the surfaces of the implant and the adjacent vertebral bodies compared to the same surface without the features or texture, thereby increasing the stability of the implant within the patient's spine. One or more of the surfaces can include a plurality of features such as sharp ridges. A featured surface can include a plurality of deforming features such as ridges, grooves, dimples, nodules, bumps, raised portions or patterns, or any combination thereof. A textured surface can have any surface roughness. In some embodiments a textured surface has a surface roughness from 1 micron to 2 mm, from 0.01 mm to 1.5 mm, from 0.1 mm to 1.5 mm, or from 0.25 mm to 1.0 mm.

Materials

The intervertebral implants provided herein, the superior and inferior surfaces, the sidewalls, etc., can be made from any suitable material having the desired mechanical properties and level of biological compatibility.

The implant, the superior and inferior surfaces, the sidewalls, the bone screws, the blades, etc., or any combination thereof can in some embodiments be made from a thermosetting polymer. Suitable thermosetting polymers include, but are not limited to, polyetherketoneketone (PEKK) and polyetheretherketone (PEEK). PEEK is particularly suitable because its modulus of elasticity closely matches that of bone. However, PEEK is also a hydrophobic material and bacteria tend to adhere easily to these types of surfaces.

In some embodiments a thermoplastic resin material, such as PEEK, is modified to increase surface hydrophobicity and/or is coated with an antibacterial agent. Biologically stable thermosetting polymers include, but are not limited to, polyethylene, polymethylmethacrylate, polyurethane, polysulfone, polyetherimide, polyimide, ultra-high molecular weight polyethylene (UHMWPE), cross-linked UHMWPE and members of the polyaryletherketone (PAEK) family, including polyetheretherketone (PEEK), carbon-reinforced PEEK, and polyetherketoneketone (PEKK). In some cases, the implant contains a substrate material, such as titanium, onto which a thermosetting polymer is coated.

The implant, the superior and inferior surfaces, the sidewalls, the bone screws, the blades, etc., or any combination thereof can in some embodiments be made from or include other suitable implantable materials, including but not limited to ceramic, titanium alloy, aluminum alloy, steel alloy, gallium, cobalt-chrome, or other materials as can be understood by one of ordinary skill in the art.

The implant, the superior and inferior surfaces, the sidewalls, the bone screws, the blades, etc., or any combination thereof can in some embodiments be formed or partially formed using additive manufacturing (e.g. 3D printing). The implant may be manufactured with an additive and/or subtractive finish to improve surface characteristics including but not limited to acid etching, addition of implant material, hydroxyapatite coating, etc.

In some embodiments, the implant material or portions thereof can be porous to mimic trabecular structure and/or to allow for osseointegration.

The blades and/or bone screws are typically made from a metal or metal alloy, such as stainless steel or titanium.

Stabilization Means

Generally, the implant contains suitable stabilization means. Suitable stabilization means secures the implant to the intervertebral space. The stabilization means can be anything capable of mechanically engaging both the implant and the adjacent vertebral bodies in a manner that stabilizes the implant in the intervertebral space. Suitable stabilization means may be mechanical elements such as blades or bone screws in various orientations. Alternatively, the stabilization means may be an adhesive such as adhesive materials or adhesive surfaces on the implant, or friction, such as due to the fit of the particular shape of the implant in the intervertebral space (e.g., friction fit, or "lock and key"). Optionally, the implant contains combination of different stabilization means. In preferred embodiments the stabilization means are bone screws, although one skilled in the art can recognize many other alternative stabilization means. These embodiments are understood to be encompassed as well.

Methods of Use

The intervertebral implants are useful for intervertebral fusion of two or more adjacent vertebral bodies, especially in the lumbar spine. Optionally, the implants are implanted in the cervical spine as part of an intervertebral fusion procedure. In addition to intervertebral fusion applications, the devices and methods described herein can also facilitate the insertion of other devices including but not limited to total disc arthroplasty devices.

In still other embodiments, the implants and methods described herein can be used for hemicorpectomy or corpectomy. As can be envisioned by one of ordinary skill in the art, the implants described herein can be useful elsewhere in the body, wherever surgical distraction is needed to separate two body parts and release tension to remove material (e.g. mandibular, ankle, or other joint surfaces).

The implant is configured for placement within an intervertebral space between the adjacent vertebrae previously occupied by a spinal disc. Following implantation, the low-profile reverse cage intervertebral implant provides stabilization and torsional resistance to promote fusion of adjacent vertebrae of the spine.

Procedures for placing intervertebral implants generally include the following steps, each of which are described in more detail below: (1) creation of an approach to the selected disc; (2) complete or partial removal of the selected disc or disc material (annulus and/or nucleus), e.g., discectomy; and (3) insertion of the intervertebral implant, optionally including placement of one or more retention devices. Removal of part of a vertebral body (hemicorpectomy), all of one vertebral body (corpectomy), or multiple vertebral bodies (corpectomies) may be reconstructed with variants of this system.

An approach through the soft tissue (i.e. skin, muscles, faciae) to a selected intervertebral disc(s) is created such that the soft tissue preferably is kept away from the site and the working area, e.g., by a retractor tool or cannula. The purpose of the approach is to provide a suitable surgical approach and exposure to the appropriate degenerative disc level.

After a suitable approach is achieved, the surgeon removes the affected disc material, such as for example the annulus, nucleus or both or portions thereof, with, e.g., curettes, or rongeurs or other instruments. The purpose of this step is to provide adequate discectomy and intervertebral endplate preparation, as well as for decompression of the spinal cord/nerve roots. As described above, this may involve hemicorpectomy, corpectomy, and/or multiple corpectomies.

After discectomy and endplate preparation, the endplates or vertebrae may be distracted to augment the intersection between the endplates and to create sufficient space for intervertebral implant. One way to perform this step is to use a distraction instrument. In some aspects, the distraction instrument includes two or more positioning rails (also referred to as placement rails) for slideably engaging the two or more positioning grooves (also referred to as placement grooves) on an implant described herein. The rails can include a vertebral contacting portion that can be used for distraction of the superior and inferior vertebrae. In some aspects, less distraction is required than would normally be required with conventional implants because the rails are sized and shaped to slideably engage the positioning grooves. This can allow for a less obtrusive installation of the implant.

Next, the surgeon inserts the intervertebral implant in the appropriate position. Proper implant placement is beneficial to ensure optimal results, including segmental motion preservation. The implant, and in particular the positioning grooves, can slideably engage the rails such that the implant can be slid along the rails and into place in the intervertebral space. It is believed that, because of the less obtrusive insertion means, the implants can be placed more easily and with a better fit, resulting in less risk of slippage or relocation after surgery and a better fit to the intervertebral space. After the implant is inserted, one or more retention means may be used to retain the implant in place in the intervertebral space and the distraction instrument may be removed. For example, one or more screws or blades can be extended through the superior and/or inferior vertebrae to engage the implant and retain the implant in place in the intervertebral space. The retention tools can include button plates and affixing tools as described below.

The intervertebral space between vertebral bodies may be approached with different techniques. Several techniques have been described, such as anterior transperitoneal, transpsoas (true lateral) or posterior approach through median incision. Another technique involves an extraforaminal approach for the insertion of spinal disc implants.

Exemplary Embodiments

Although the invention is illustrated and described herein with reference to various specific embodiments, the invention is not intended to be limited to the details of the particular embodiments. Therefore, while various modifications may be made in the details and within the scope and range of equivalents of the claims, these are not departing from the invention. The specific embodiments described herein are to be regarded as "illustrative of" the intervertebral implants.

Anterior Cervical Discectomy and Fusion (ACDF) Implant

FIGS. 2A-2C depict exemplary aspects of an ACDF implant 200. FIG. 2A is a perspective view of the exemplary cervical ACDF implant from the anterior view. FIG. 2B is a side view of the exemplary cervical ACDF implant. FIG. 2C is a top view of the exemplary cervical ACDF implant. The implant 200 has a superior implant surface 201 having a first superior positioning groove 211 and a second superior positioning groove 212. The implant 200 has an inferior implant surface 202 having a first inferior positioning groove 221 and a second inferior positioning groove 222. The superior implant surface 201 is configured for engaging a superior vertebral surface when the implant is implanted in the intervertebral space. Likewise, the inferior implant surface 202 is configured for engaging an inferior vertebral surface when the implant is implanted in the intervertebral space. In some embodiments, such as for anterior cervical applications, the implant can have an anterior-posterior length of about 11 mm to 14 mm or about 11 mm, a mediolateral width of about 10 mm to 16 mm or about 12 mm, and a height at the anterior wall of about 4 mm to 100 mm. In the depicted embodiment, the anterior wall has a height of about 4 mm to 14 mm.

The superior implant surface 201 and inferior implant surface 202 are separated by a plurality of sidewalls, e.g. an anterior wall 232 and a posterior wall 231 along with a first side wall 233 and a second side wall 234. One or more cutouts 240 in the sidewalls can allow access to the central void space 241 once the implant 200 is in place in the intervertebral space, e.g. for packing bone growth material and bridging bone for lateral fusion.

Figure 3:
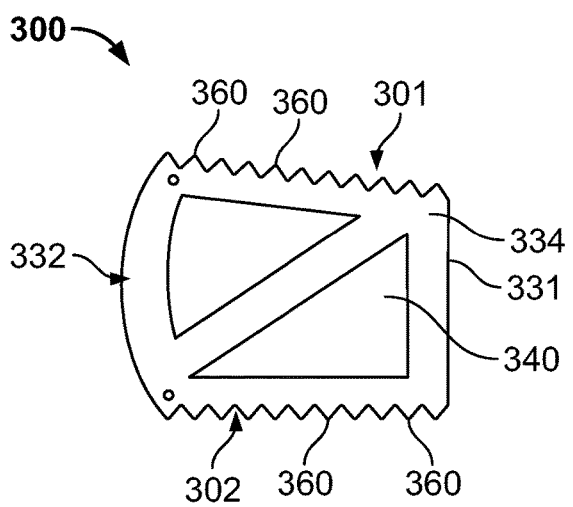
FIG. 3 is a side view of a second exemplary anterior cervical discectomy and fusion (ACDF) implant having a curvature to match the lordotic curvature of the cervical spine and a textured superior and inferior surface.

FIG. 3 depicts second exemplary cervical ACDF implant 300 where the posterior wall 331 is shorter than the anterior wall 332 and the anterior wall 332 has a slight curvature to better accommodate the lordotic curvature of the cervical spine. The posterior wall 331 can be about 2 mm to 4 mm shorter than the anterior wall 332, or about 4 mm to 98 mm. The superior surface 301 and the inferior surface 302 can have an angulation between them, which can be approximately 6 degrees for anterior cervical applications, but other dimensions can be envisioned for different applications. The superior surface 301 and the inferior surface 302 include a plurality of deforming features 360 creating a textured or irregular surface for improved retention in the intervertebral space. The side wall 334 also includes one or more cutouts 340 in the side walls, e.g. for packing bone growth material.

Figure 4:
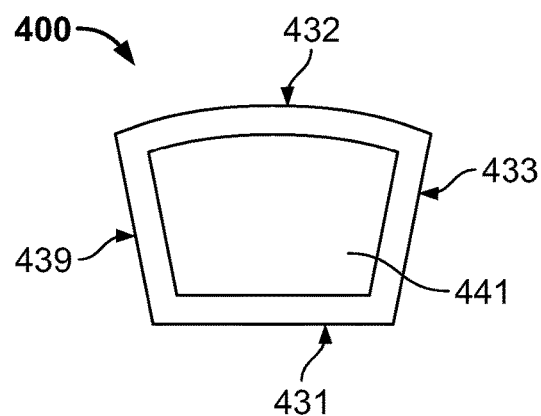
FIG. 4 is a top view of a third exemplary anterior cervical discectomy and fusion (ACDF) implant having a contour to match the vertebral body.

FIG. 4 depicts a top view of a third exemplary cervical ACDF implant 400 where the anterior wall 432 is contoured to better match the contour of the vertebral body, and the first side wall 433 and second side wall 434 taper from the anterior wall 432 to the posterior wall 431 Although the depicted posterior wall 431 is flat, however the wall can also be concave or otherwise shaped to accommodate the anatomy of a particular application. A central void space 441 can be present e.g. for packing bone growth material and bridging bone for lateral fusion once the implant 400 is in place. In other embodiments, the implant may be solid and/or textured, without a bone growth void. Although not depicted, cervical ACDF implant 400 can include one or more superior positioning grooves 411.

Figure 5:
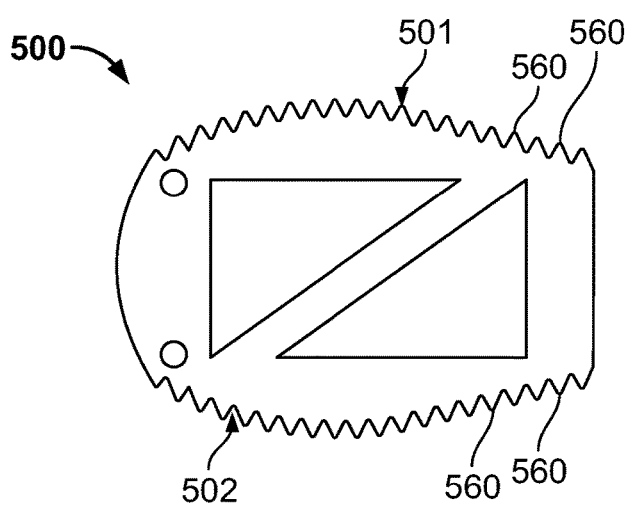
FIG. 5 is a side view of a fourth exemplary anterior cervical discectomy and fusion (ACDF) implant having a convex superior and inferior surface.

FIG. 5 depicts a side view of a fourth exemplary cervical ACDF implant 500 where both the superior surface 501 and the inferior surface 502 are convex (referred to as a "biconvex implant") and have a plurality of deforming features 560 creating a textured or irregular surface for improved retention in the intervertebral space. Although not depicted, cervical ACDF implant 500 can include one or more superior positioning grooves 511.

Cervical Corpectomy Cage

FIG. 6A is a side view of the exemplary corpectomy implant 600. FIG. 6B is a top view of the exemplary corpectomy implant 600. The anterior wall 632 can be about 14 mm to 100 mm high. Anterior wall 632 and/or posterior wall 631 can be contoured. The first side wall 633 and second side wall 634 taper outward from the anterior wall 632 to the posterior wall 631. In other embodiments, the implant 600 can also taper in width anteriorly to posteriorly. The superior surface 601 and the inferior surface 602 include a plurality of deforming features 660 creating a textured or irregular surface for improved retention in the intervertebral space. The superior implant surface 601 can have a first superior positioning groove 611 and a second superior positioning groove 612. The implant 600 can have an inferior implant surface 602 having a first inferior positioning groove 621 and a second inferior positioning groove 622. In some embodiments, there can be single superior and inferior positioning grooves.

Thoracolumbar and Interbody Fusion Implants

Figure 7B:
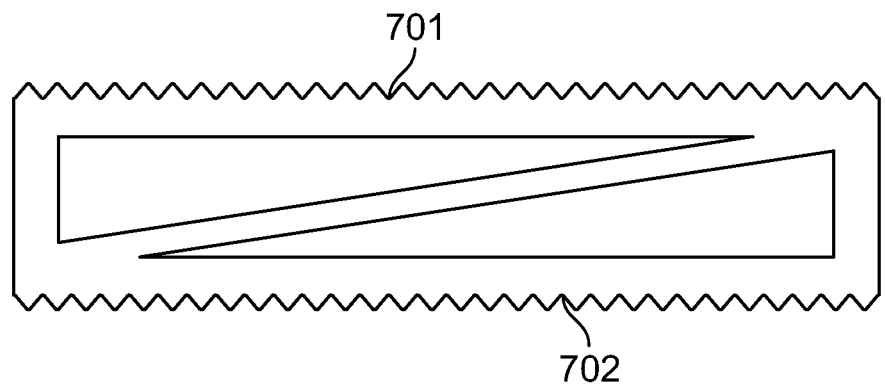
Figure 7C:
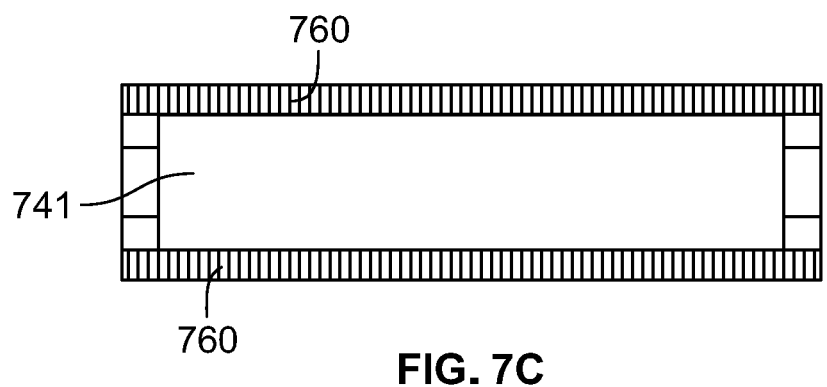

FIGS. 7A-7C depict an exemplary thoracolumbar implant designed for a lateral approach. The implant 700 has a superior implant surface 701 having a first superior positioning groove 711 and a second superior positioning groove 712. The implant 700 has an inferior implant surface 702 having a first inferior positioning groove 721 and a second inferior positioning groove 722. FIG. 7A is an anterior perspective view of the exemplary thoracolumbar implant. A multifunctional window 741 functions as a large port or graft window and can be present e.g. for packing bone growth material after insertion. Radiopaque markers 750 can be included. FIG. 7B is a side view of the exemplary thoracolumbar implant. In this example, both the superior surface 701 and the inferior surface 702 are flat. FIG. 7C is a top view of the exemplary thoracolumbar implant, showing deforming features 760 creating a textured or irregular surface for improved friction and/or retention. Said deforming features 760 can be included on one or both of superior implant surface 701 and inferior surface 702. Multifunctional window 741 can also be seen from the top view. The implant can have a mediolateral length of about 30 mm to 60 mm, an anterior-posterior width of about 10 to 20 mm, and a height at the anterior wall of about 4 mm to 20 mm.

The positioning grooves can also be used to aid in the accurate placement of instrumentation such as anterior plates.

Figure 8:
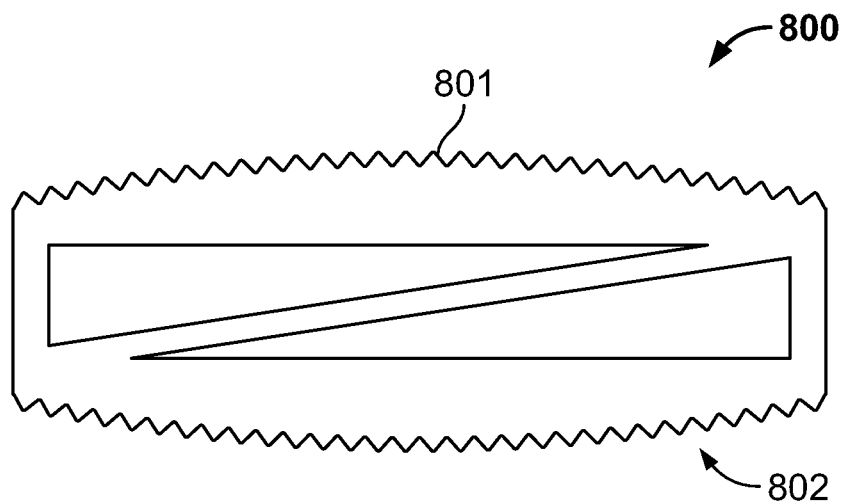
FIG. 8 is a side view of a second exemplary thoracolumbar implant.

FIG. 8 is a side view of a second exemplary thoracolumbar implant. In this example, both the superior surface 801 and the inferior surface 802 are convex. The biconvex shape is an alternative embodiment to flat shapes such as in FIGS. 7A-7C to accommodate different endplate shapes and or a surgeon's preference. The implant can have a mediolateral length of about 30 mm to 60 mm, an anterior-posterior width of about 10 to 20 mm, and a height at the anterior wall of about 4 mm to 20 mm.

Figure 9A:
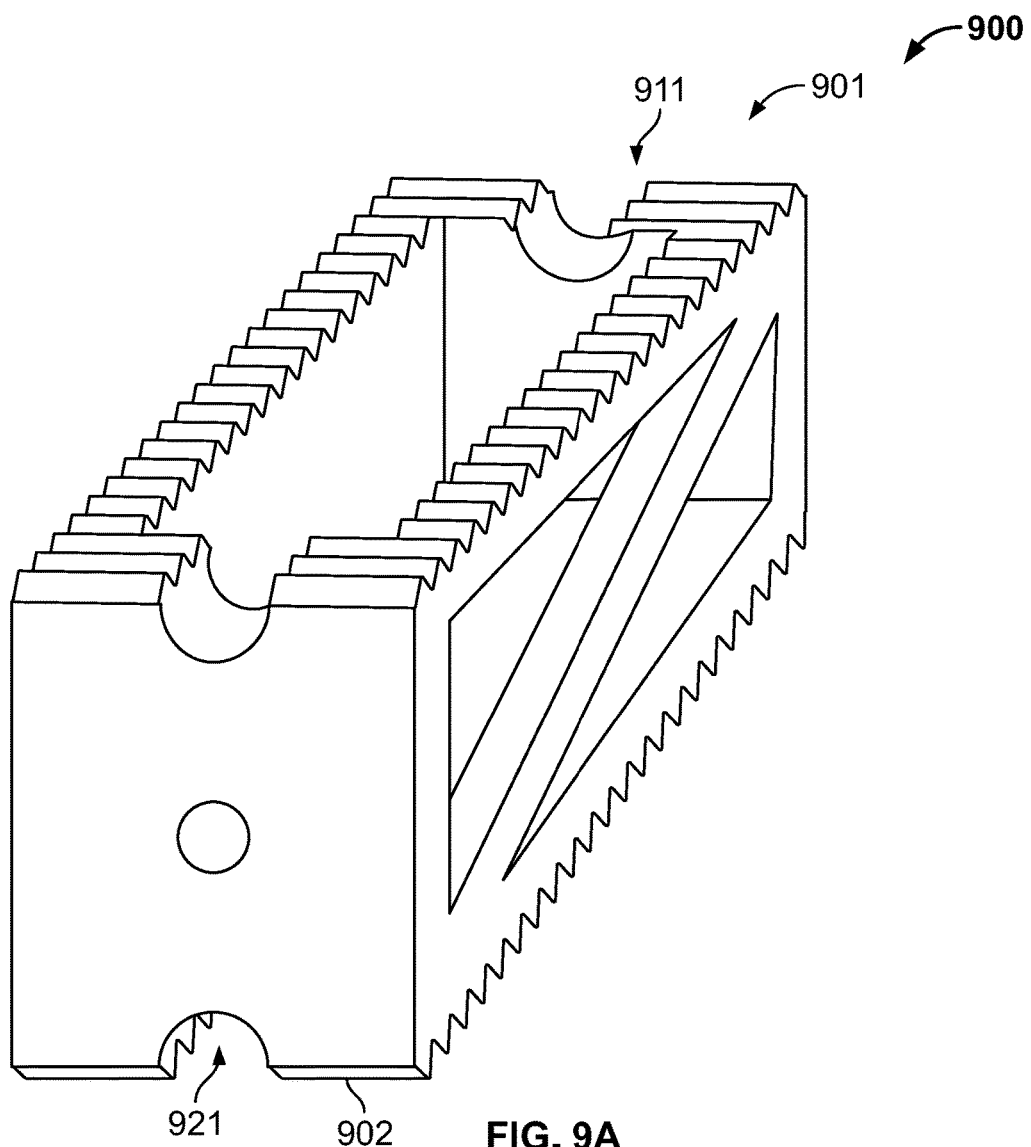
FIGS. 9A-9B depict an exemplary posterior lumbar interbody fusion (PLIF) implant.
Figure 9B:
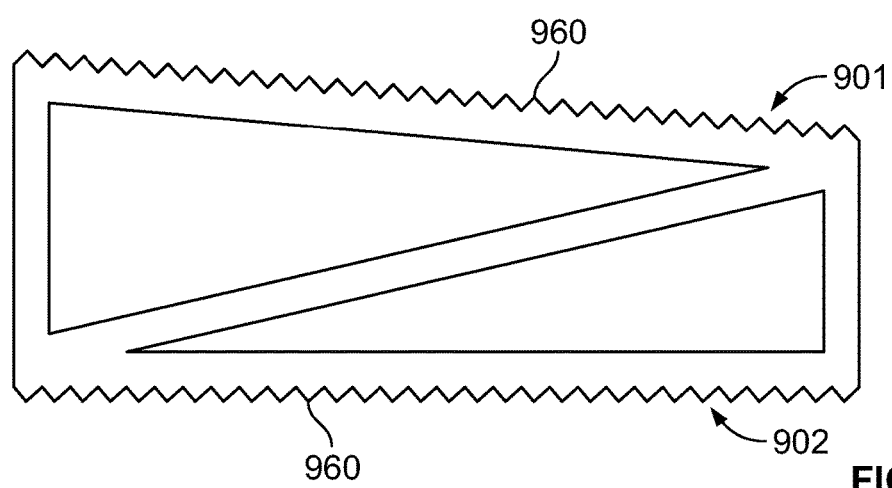

FIGS. 9A-9B depict an exemplary posterior lumbar interbody fusion (PLIF) implant. FIG. 9A is a perspective view of the exemplary PLIF implant. The implant 900 has a superior implant surface 901 having a single superior positioning groove 911 and an inferior implant surface 902 having a first inferior positioning groove 921. The single positioning groove allows for insertion with a monorail tool. FIG. 9B is a side view of the exemplary PLIF implant showing optional deforming features 960 creating a textured or irregular surface for improved friction and/or retention. Said deforming features 960 can be included on one or both of superior implant surface 901 and inferior surface 902. The anterior wall can be taller than the posterior wall to create a tapered device. The implant can have an anterior-posterior length of about 15 mm to 30 mm, a mediolateral width of about 8 to 15 mm, and a height at the anterior wall of about 4 mm to 20 mm.

Figure 10:
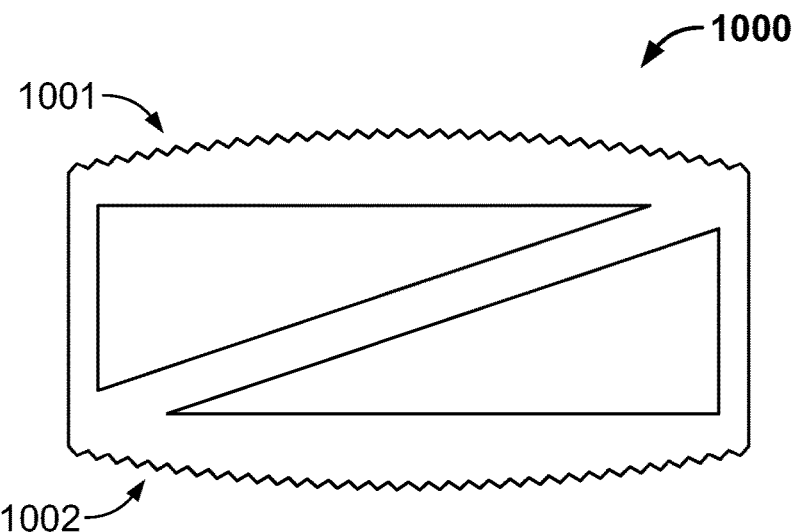
FIG. 10 is a side view of a second exemplary PLIF implant.

FIG. 10 is a side view of a second exemplary PLIF implant having biconvex superior and inferior surfaces to mimic the disc shape in the L4-S1 region where a PLIF implant is typically used. Although not depicted, the implant 1000 has a superior implant surface 1001 having a single superior positioning groove 1011 and an inferior implant surface 1002 having a first inferior positioning groove 1021. The implant can have an anterior-posterior length of about 15 mm to 30 mm, a mediolateral width of about 8 to 15 mm, and a height at the anterior wall of about 4 mm to 20 mm. In some embodiments, the anterior and posterior heights can be different from one another.

Figure 11A:
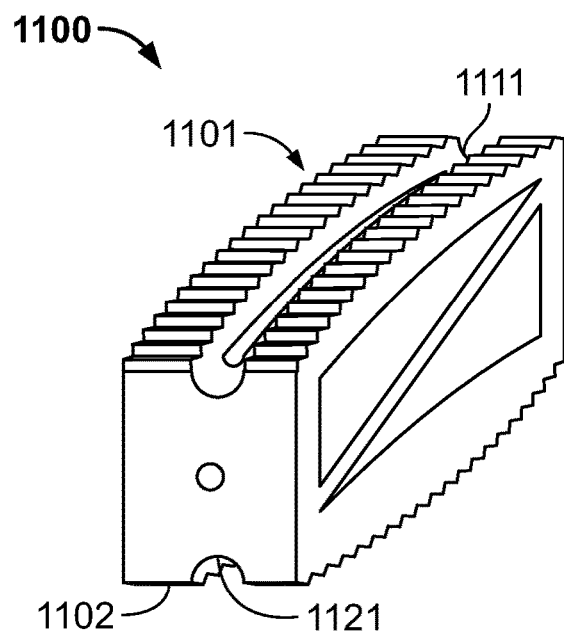
FIGS. 11A-11B depict an exemplary transforaminal lumbar interbody fusion (TLIF) implant.
Figure 11B:
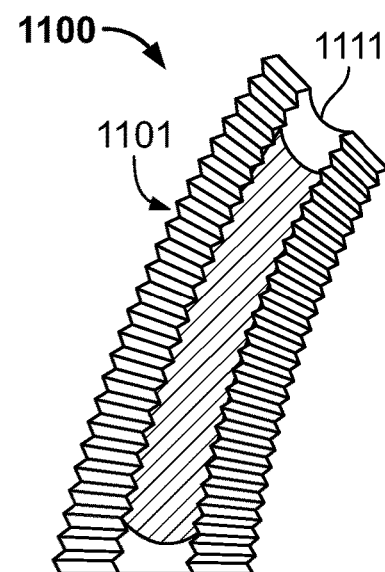

FIGS. 11A-11B depict an exemplary transforaminal lumbar interbody fusion (TLIF) implant. FIG. 11A is a perspective view of the exemplary TLIF implant 1100. The implant 1100 has a superior implant surface 1101 having a single superior positioning groove 1111 and an inferior implant surface 1102 having an inferior positioning groove 1121. The TLIF implant 1100 can have a superior curved profile. The single positioning groove allows for insertion with a monorail tool. The prong of said monorail tool can be a small protrusion configured to fit into the groove (not shown) or solitary prong for insertion into the superior and inferior positioning grooves 1111 and 1121. FIG. 11B is a top view of the exemplary TLIF implant. The TLIF superior positioning groove 1111 and the inferior positioning groove 1121 can be mediolaterally curved. A distractor/caliper positioning tool including a pin in place of a positioning rail can facilitate positioning by allowing the implant to turn along the grooves as it is inserted. As described in previous embodiments, the TLIF implant 1100 could also include deforming features on one or both of superior implant surface 1101 and inferior implant surface 1102. The implant can have an anterior-posterior length of about 15 mm to 30 mm, a mediolateral width of about 8 to 15 mm, and a height at the anterior wall of about 4 mm to 20 mm.

Anterior Lumbar Interbody Fusion (ALIF) Implants

Figure 12A:
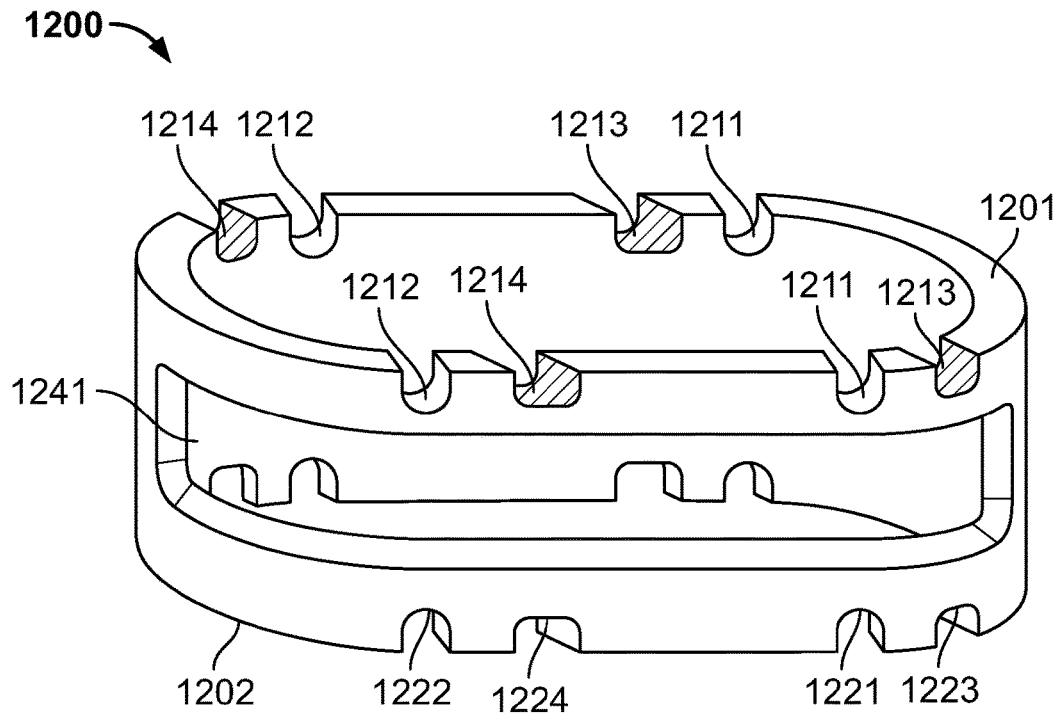
FIGS. 12A-12B depict an exemplary anterior lumbar interbody fusion (ALIF) implant.
Figure 12B:
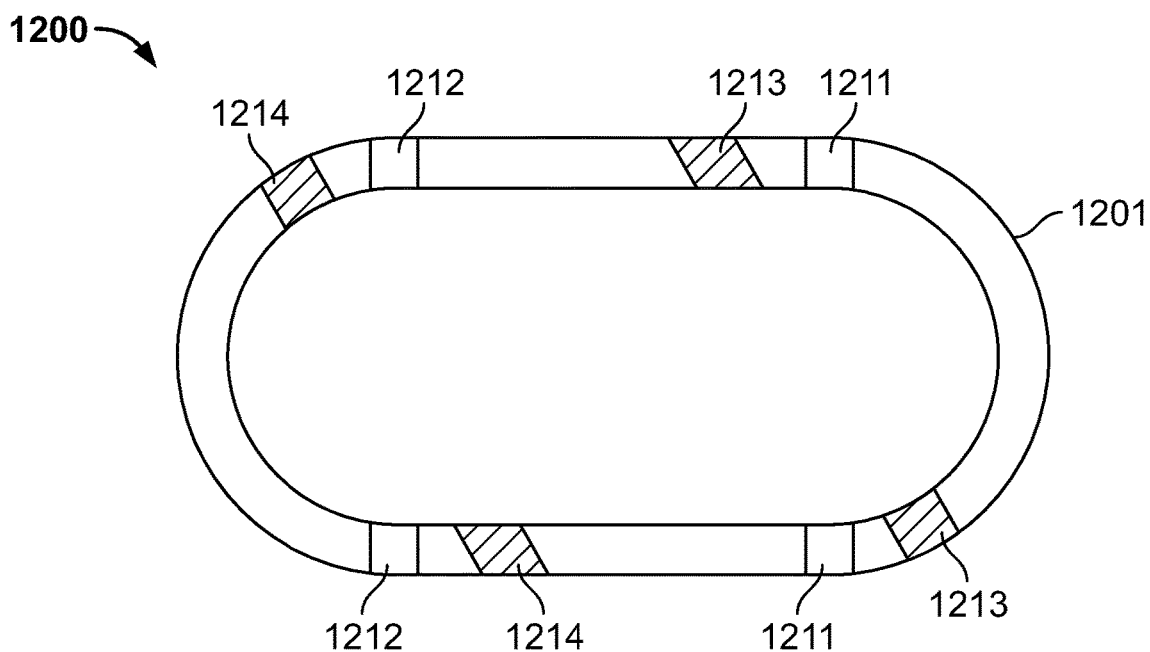

FIGS. 12A-12B depict an exemplary anterior lumbar interbody fusion (ALIF) implant. The depicted implant can also be used for oblique anterior insertion. The implant 1200 has a superior implant surface 1201 having a first superior positioning groove 1211 and a second superior positioning groove 1212, along with oblique positioning grooves 1213 and 1214. The implant 1200 has an inferior implant surface 1202 having a first inferior positioning groove 1221 and a second inferior positioning groove 1222, along with oblique positioning grooves 1223 and 1224. The oblique positioning grooves are wider than the corresponding positioning grooves 1211, 1212, 1221, and 1222 to allow for oblique cage insertion to accommodate the vena cava. For example, the diameter of the superior and inferior positioning grooves can be about 1.5 mm, and the oblique positioning grooves can have a diameter of about 2 mm. A central void space 1241 functions as a large port and can be present e.g. for packing bone growth material after insertion. In the figure, the oblique positioning grooves on the superior side are hashed to distinguish them from the superior positioning grooves. FIG. 12A is an anterior perspective view of the exemplary ALIF implant. FIG. 12B is a top view of the exemplary ALIF implant.

Figure 12C:
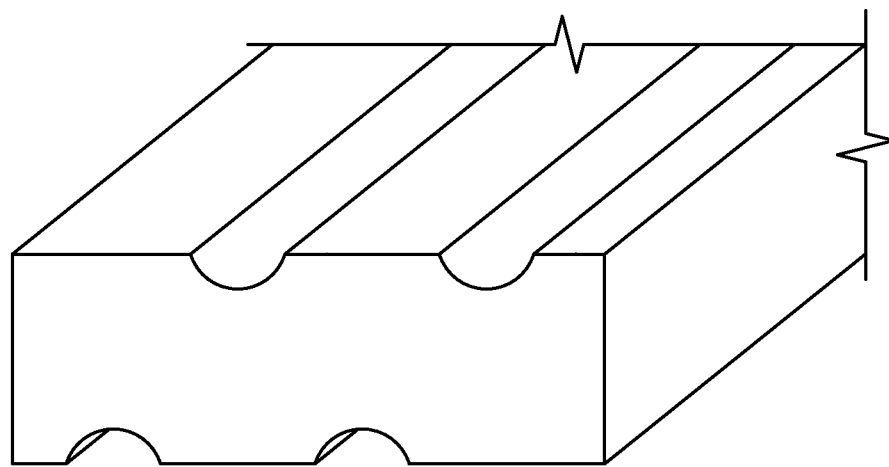
FIGS. 12C, 12D, and 12E provide additional examples of possible positioning rail placement.
Figure 12D:
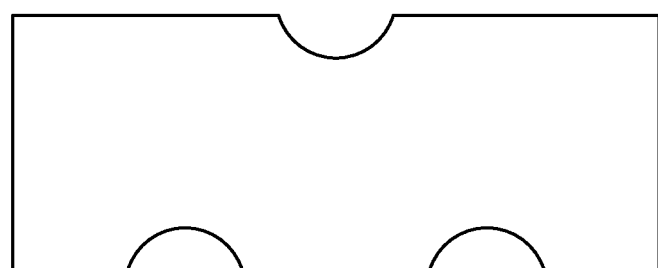
Figure 12E:
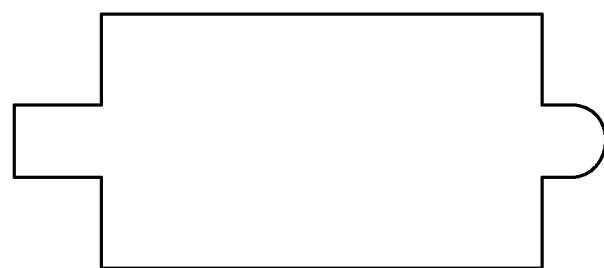

FIGS. 12C-12E are additional non-limiting examples of possible positioning groove arrangements. Corresponding positioning rails on a positioning tool can be used. FIG. 12C shows an embodiment in which paired superior and inferior positioning grooves are offset from one another. FIG. 12D shows an embodiment in which there are an unmatched number of superior and inferior positioning grooves. In this particular embodiment, there is a single superior groove and a pair of inferior grooves. FIG. 12E provides an embodiment in which paired positioning grooves are on the lateral edges of the implant, rather than the superior and inferior location of the other shown embodiments.

Implant Systems Including Positioning Tools

Distractor-Caliper Positioning Tools

Positioning tools, such as a distractor (also distractor-inserter or distractor-caliper), can be used in conjunction with the implants described herein. The positioning tool can serve multiple functions. The positioning tool can include one or more positioning rails that correspond to the positioning grooves on the implants as described above, acting similarly to a forklift for insertion of the implant upon distraction. The positioning rails can also function as a retractor to separate bone or tissues. In some embodiments, the positioning tool can include a caliper scale, such that measurements can be taken and/or the tool arms can be locked open at a specific width.

The positioning tool can be modular, having a handle portion corresponding to at least one removable attachment. The removable attachments can have various configurations that correspond to the implant shapes described above. The attachments can be interchangeable, selected based on the type of implant needed. Advantageously, the overall cost of the implant system can be lowered, and the flexibility of the surgeon increased. For example, the implant can be provided to the user with the appropriate attachment, allowing for a one-time tool purchase of the handle. Alternatively, the handle can be provided with a set of attachments such that the user can select from any number of implants and have the appropriate tool. In some embodiments, the handle portion can be a clamp-type tension handle having two crossed arms, such that when user squeezes the handles together, the arms spread apart. An attachment having positioning rails can be attached to each arm, the number and configuration of the positioning rails selected to correspond to the positioning grooves of a selected implant. Alternatively, the handle portion can be similar to a rib spreader.

Figure 13A:
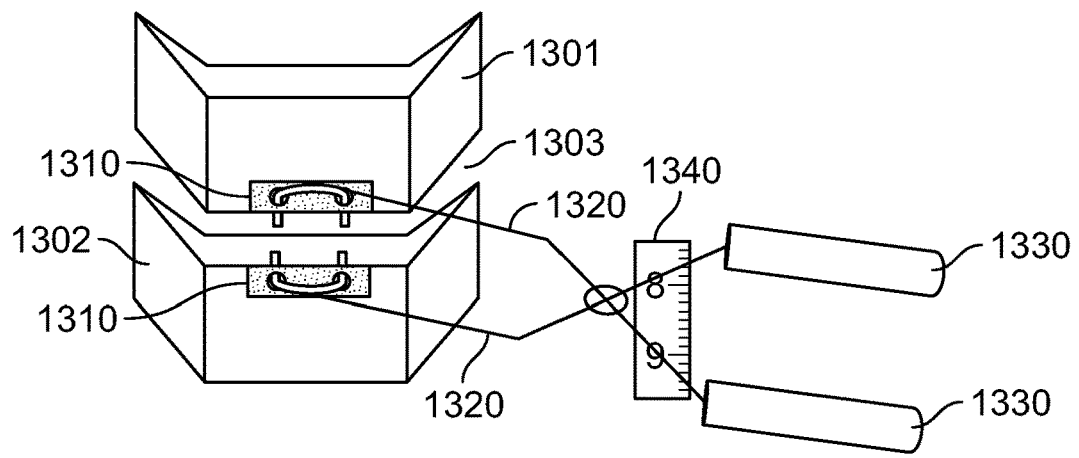
FIG. 13A depicts an exemplary positioning tool having removable attachments.

FIG. 13A depicts a possible embodiment of a positioning tool 1300 having removable attachments. The figure shows positioning tool 1300 as a distractor-caliper separating superior vertebra 1301 from inferior vertebra 1302 to create an intervertebral space 1303 held open by attachments 1310 and arms 1320. Handles 1330 have been pressed together, causing arms 1320 to widen. Arms 1320 can be locked into place using an incremental locking mechanism such as teeth, a ratcheting mechanism, or the like, and the distance measured using the scale 1340.

Figure 13B:
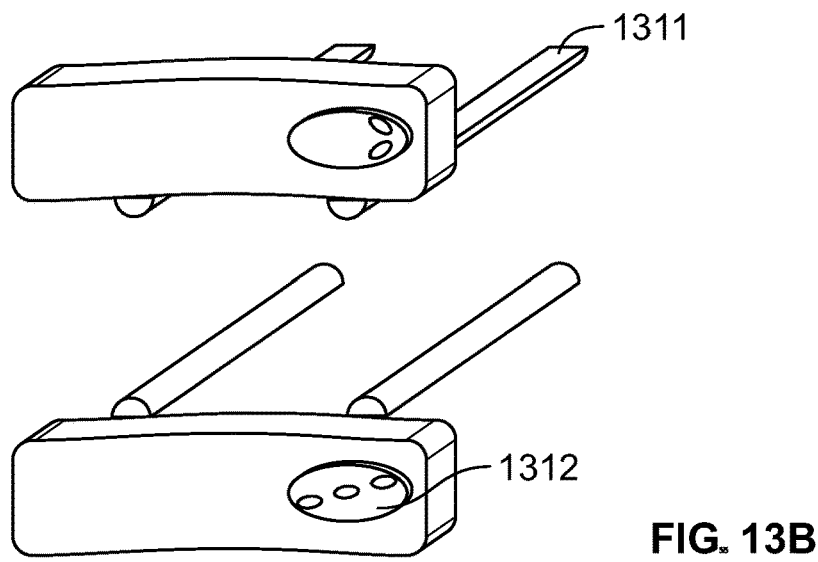
FIGS. 13B-13E depict embodiments of the removable attachments.
Figure 13C:
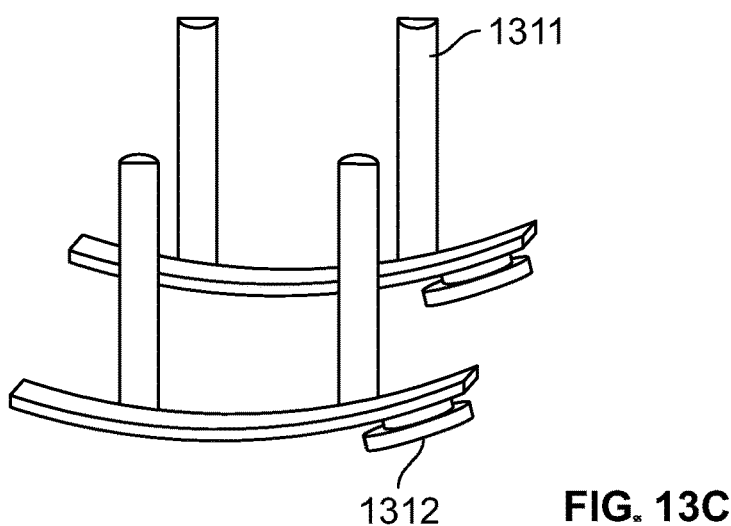
Figure 13D:
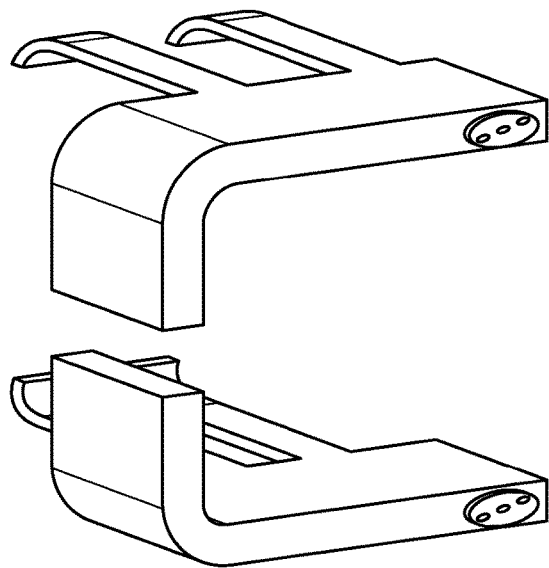

FIGS. 13B-13D depict embodiments of attachment 1310. Shown are pairs of attachments 1310, one for each arm 1320 shown in FIG. 13A. Attachment 1310 can have one or more positioning rails 1311. The depicted embodiments show two positioning rails 1311 per attachment 1310. However, in some embodiments, the positioning tool can have a single positioning rail 1311 on each attachment 1310 (e.g. for an implant such as shown in FIG. 9A or 11A). The body of attachment 1310 can have a flange 1312 to lock the attachment to the positioning tool arms 1320. The attachment 1310 shown in FIG. 13C is curved to fit the spine and align the positioning rails 1311 to the corresponding positioning grooves on a selected implant. In some embodiments (not shown), the positioning rails can be offset to accommodate non-orthogonal positioning of the implant. FIG. 13D depicts another possible embodiment, in which the body of the attachment 1310 is lipped to follow the contours of a curved implant, such as a TLIF (FIG. 11A). The positioning rails depicted have a half-cylindrical shape, but the positioning rails may have a cylindrical shape or other shape as can be envisioned by one of ordinary skill in the art, and can be coupled with positioning grooves having an inverse profile.

Figure 13E:
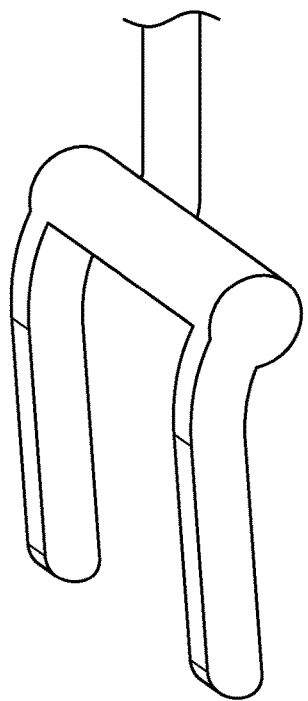
Figure 13F:
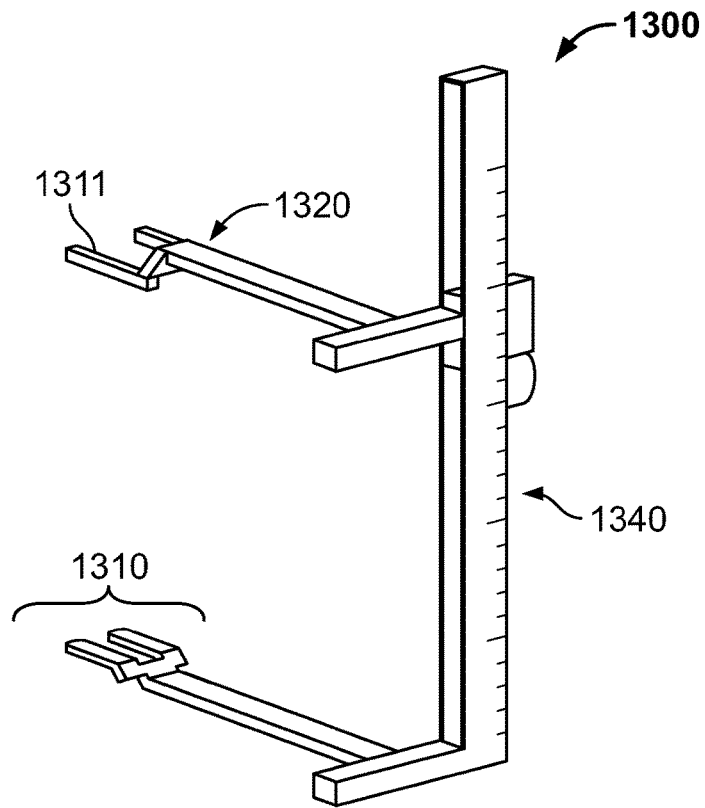
FIG. 13F is another possible embodiment of the positioning tool or distractor-caliper.

FIG. 13E is another possible embodiment of the positioning tool or distractor-caliper 1300.

As described in reference to FIGS. 13B and 13C, a flange can lock the attachment to a corresponding slot on the arm of the positioning tool. In other embodiments, the flange can be located on the arms and a corresponding slot can be located on the attachment. The attachments can be attached by a variety of other means as can be envisioned by one of ordinary skill in the art.

In other embodiments, the positioning tool is not modular, and each implant type has a specific tool with corresponding positioning rails.

Plates for Stabilization Means

As described above, stabilization means such as bone screws or blades can be used to affix the implant. The implant system can include stabilization plates and affixing tools to assist in screw and/or blade placement. The stabilization plate 1400 (FIGS. 14A and 14B) can have apertures 1410 for screw placement, with one or more protrusions 1420 (or buttons) for placement and alignment. The stabilization plate 1400 shown in FIG. 14A is a lateral lumbar plate that can be used in conjunction with a thoracolumbar implant (such as FIG. 7A). The stabilization plate 1400 shown in FIG. 14B is a cervical plate that can be used in conjunction with an implant such as shown in FIG. 2A or 6A. The stabilization plate 1400 advantageously can fit onto a corresponding implant such that the plate is prevented from sliding during installation. The plate 1400 shown in FIG. 14A can also close the graft widow sealing the central void space. The multifunctional window 741, such as shown in FIG. 7A, of the implant is configured to receive the protrusion 1420 on the stabilization plate 1400 and also the impaction tool (such as FIGS. 16A and 16B). The affixing tool 1500 can include one or more awls 1510 or prongs that correspond to the apertures 1410 in the button plate (FIG. 15A) and one or more receptacles 1520 to receive the protrusions 1420 (FIG. 15B), such that the affixing tool and the button plate fit together to ensure that the awl punctures the bone in the location of the apertures. The affixing tool 1500 can have a handle 1530 and can be used in conjunction with a mallet or other striking instrument to puncture the bone. The affixing tool 1500 can be used to puncture the bone to create starter holes for insertion of bone screws. The button receptacle 1520 can be used to assist the surgeon with picking up the button plate 1400 for placement.

Impaction Tools

Figure 16A:
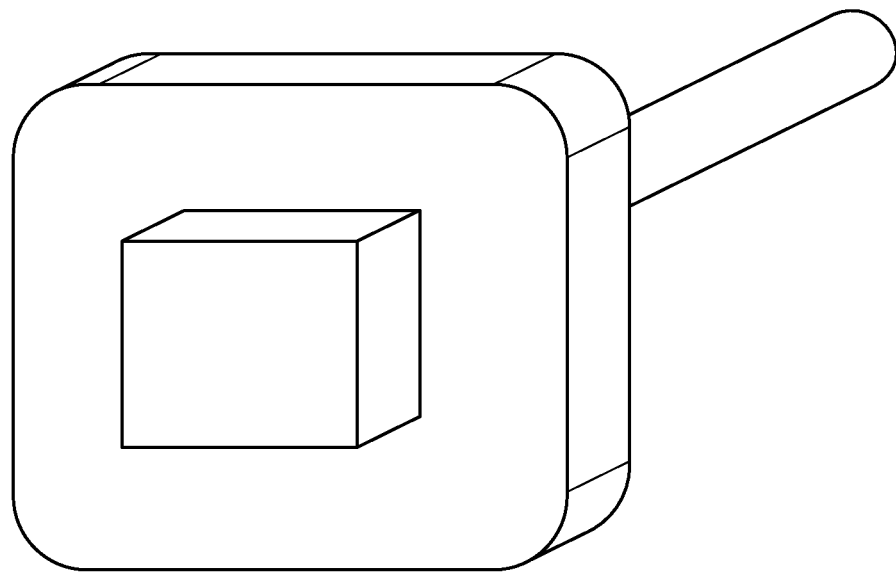
FIGS. 16A and 16B are examples of an impaction tool.
Figure 16B:
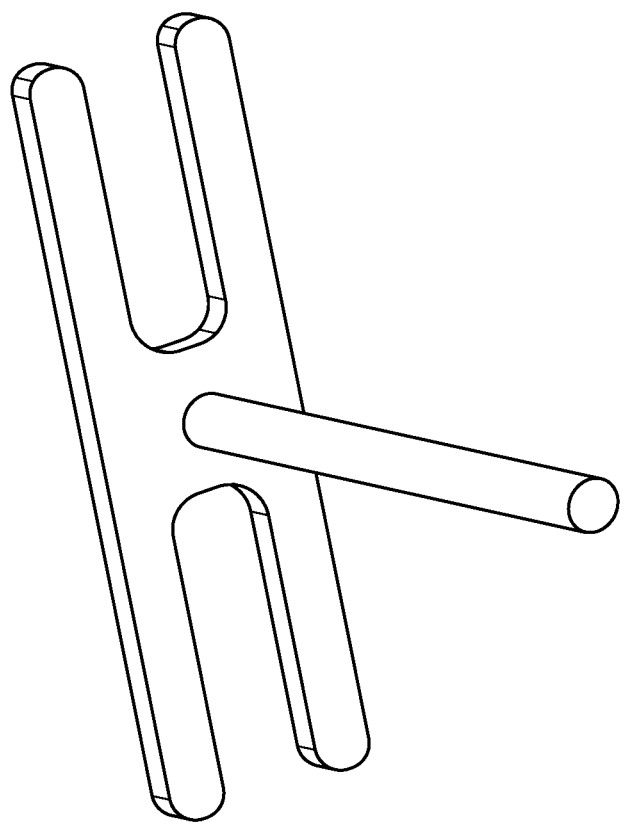

FIGS. 16A and 16B are examples of an optional impaction tool to allow for graft material insertion into an implant after the implant is in situ. Generally, bone graft material is packed into an implant prior to placement in a patient because it is difficult to pack the implant in place without disrupting the position of the implant with the force of impaction. The impaction tools provided herein are designed to mate specifically with the implants such that the graft material can be packed while the implant is in place while allowing for controlled force by the surgeon and reducing the risk of over-impaction. For example, the impaction tool shown in FIG. 16A includes a protrusion (or button) configured to mate with the multifunctional window 741 of an implant such as the one shown in FIGS. 7A-7C. In another example (FIG. 16B), the impaction is performed by a stem configured to mate with the hole leading to the central void space, such as shown in FIGS. 2A, 9A, and 11A. This embodiment can include safety rails, shown here having an "H" shape, which straddle the positioning rails of the positioning tool 1300.

Advantageously, the stabilization plates, impaction tools, positioning tools, and implants described herein are designed to work in conjunction with one another as a system. The combination of these system components allows for impaction of the graft material after positioning of the implant without graft material spillage. Existing implants are difficult to fill in situ without risking over-impaction. Through the combination of complimentary impaction and positioning tools with the implants, the systems described herein prevent over-impaction and provide the surgeon with control and can mitigate force during insertion. The stabilization plate is configured to receive the implant to prevent movement or migration of the plate during screw placement. The distractor-caliper positioning tool provides for a removable distractor without disturbing the implant. The components of the system can work in concert to aid in determining size of the implant, placement of the implant, packing of graft material, positioning of screws, and preventing damage to surrounding structures.

The Structure of Intervertebral Discs and Implants

There are typically 24 intervertebral discs in the human spine, interspersed between the vertebral bodies. The intervertebral discs can be identified by the two adjacent vertebrae, so the C6-C7 intervertebral disc lies between the two most inferior of the cervical vertebrae whereas the T12-L1 intervertebral disc lies between the inferior thoracic vertebra and the superior lumbar vertebra. The intervertebral discs generally increase in size moving down the spine, to approximately 45 mm antero-posteriorly, 64 mm laterally and 11 mm in height in the lumbar region.

The majority of disc herniation occurs in the lumbar spine, typically (~95%) in L4-L5 or L5-S1. The cervical spine is the second most common site of spinal disc herniation, typically at C5-C6 or C6-C7. Thoracic disc herniation is the least common, occurring in less than 4% of cases.

The lumbar vertebrae graduate in size from L1 through L5. The mediolateral distance in the lumbar spine ranges from roughly 30-70 mm, with average values around 50 mm. The anteroposterior distance ranges from approximately 20-55 mm, with typical values around 35 mm.

The wedge angles (i.e., the angle between the superior and inferior surface of the intervertebral disc) typically graduate moving down the lumbar spine, increasing from 4°-10° as typical values for L1-L2 intervertebral discs to 12°-16° as typical values for L5-S1 intervertebral discs. The average wedge angle in the lumbar spine increases with age, the average across all levels of the lumbar discs being less than 10° below age 30 and increasing to over 15° beyond age 50. The average wedge angle observed from MRI and X-ray of the intervertebral space of 73 patients for TI2-LI is roughly 4°-5°, for L1-L2 is 5°-6°, for L2-L3 is 5.5°-6.5°, for L3-L4 is 6°-7°, for L4-L5 is 8°-10°, and for L5-S1 is 12°-14°. See Mark Eijkelkamp. On the Development of an Artificial Intervertebral Disc Diss., The University of Groningen, Groningen, Netherlands, 2002 and the references cited therein.

Sometimes intervertebral heights (height between the superior vertebral surface a and the inferior vertebral surface b) are reported as a single value that can be the medial height or that can be an average of the anterior and posterior height as will be apparent by context. One or more heights can also be reported as a range of values, such as a range of values observed for the different intervertebral spaces within a patient or as a range of values observed for a particular intervertebral space observed across a range of patients.

The height in the anterior region for T12-L1 was observed to be approximately 8-10 mm (average 9 mm), for L1-L2 approximately 9-12 mm (average 10.5 mm), for L2-L3 approximately 10-15 mm (average 12 mm), for L3-L4 approximately 10-16 mm (average 13 mm), for L4-L5 approximately 12-16 mm (average 14 mm), and for L5-S1 approximately 9-16 mm (average 13.5 mm). The medial heights range typically from 8-10 mm (average 9 mm) for T12-LI, 10-12 mm (average 11 mm) for L1-L2, from 11-16 mm (average 13 mm) for L2-L3, from 11-17 mm (average 14) for L3-L4, from 12-16 mm (average 13 mm) for L4-L5, and from 9-13 mm (average 11 mm) for L5-S1. There is less variation in the posterior heights. The heights in the posterior region observed in the same population ranged from 5-8 mm (average 6.5 mm) for T12-L1, from 6-9 mm (average 7.5 mm) for L1-L2, from 7-12 mm (average 9 mm) for L2-L3, from 7-13 mm (average 10 mm) for L3-L4, from 7-11 mm (average 9 mm) for L4-L5, from 5-9 mm (average 7 mm) for L5-S1. See Mark Eijkelkamp. *On the Develop-*

*ment of an Artificial Intervertebral Disc* Diss., The University of Groningen, Groningen, Netherlands, 2002 and the references cited therein.

Based on measurements such as those provided above, the implants described herein can be manufactured to appropriate dimensions to accommodate the average patient for specific anatomical locations. In a non-limiting example, the dimensions of an implant for a T12-L1 implant may have an anterior wall height of 7 mm to 10 mm, whereas an implant for L4-L5 may have an anterior wall height of 11 mm to 16 mm In alternative embodiments, the implants can be bespoke for a particular patient, such as via 3D printing based on measurements obtained through imaging prior to surgery.

Methods for Use

The implants and systems described herein can be used during patient surgery to optimize the amount of force required to insert the implant when compared with traditional methods, as well as allowing for more controlled distraction and insertion. The method can include performing a discectomy or corpectomy on a subject in which a positioning tool that functions as both a distraction instrument and an implant positioning tool is inserted between adjacent vertebrae. The positioning tool can include two or more positioning rails. In some embodiments, the positioning tool is a combination distractor caliper, as described above. The positioning tool can be used to enlarge an intervertebral space and locked. The scale can then be used to determine the appropriately sized spinal implant. The spinal implant can be slidably engaged into the intervertebral space. The intervertebral implant includes one or more positioning grooves configured to receive a corresponding positioning rail from the positioning rails on the positioning tool. The positioning tool can then be slidably removed from the intervertebral space along the positioning grooves without disturbing the implant.

The method can include packing graft material into the central void of the implant while the implant is in situ. In some embodiments, the implant can include a multifunctional window leading to a central void in the implant. An impaction tool having a complementary shape and size to mate with the multifunctional window can be used to pack the central void.

The method can further include stabilizing the implant. Stabilizing placing a stabilization plate on the bone to retain the implant's position. The stabilization plate is configured to mate with the implant such that when it is placed, the stabilization plate is oriented correctly and stays in position while it is adhered to the bone (e.g. by screws). An affixing tool having puncturing means (e.g. one or more awls) that correspond to apertures in the stabilization plate can be used to puncture accurately placed holes for the screws. The plate can then be adhered to the bone, such as by screwing the plate in.

In some embodiments one or more of the positioning grooves is located on a superior implant surface and one or more of the positioning grooves is located on an inferior implant surface. The positioning tool can have rails corresponding to the positioning rail.

The spinal implant can be selected from any of the implants described above, including but not limited to an anterior cervical discectomy and fusion implant, an anterior cervical corpectomy implant, a thoracolumbar implant, a posterior lumbar interbody fusion implant, a transforaminal lumbar interbody fusion implant, or an anterior lumbar interbody fusion implant.

In some embodiments, one or both of the superior implant surface and the inferior implant surface comprise a feature and/or a textured surface that increases the frictional resistance between that surface of the implant and the adjacent vertebrae compared to the same surface in the otherwise same implant except without the features or texture.

In some embodiments, one or both of the superior implant surface and the inferior implant surface comprise a convex surface.

In some embodiments, each of the superior and inferior positioning grooves can have a length of about 8 mm to about 60 mm, a diameter perpendicular to the length, wherein the diameter is about 1.5 mm to 2.0 mm, and wherein a length of each of the corresponding positioning rails is less than or equal to the length of the superior and inferior positioning grooves.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

I claim:

1. A cervical spinal implant, the implant comprising:
   a superior implant surface, wherein the superior implant surface comprises one or more superior positioning grooves having a shape corresponding to and a size larger than a superior positioning rail, wherein the superior and inferior positioning grooves have a length of about 8 mm to about 60 mm and a diameter perpendicular to the length of about 1.5 mm to 2.0 mm, wherein the superior positioning grooves slidably engage a corresponding superior positioning rail such that the implant can be slid along the positioning rail and into place in an intervertebral space and such that the corresponding superior positioning rail can be slidably removed from the intervertebral space along the positioning grooves without disturbing the implant;
   an inferior implant surface, wherein the inferior implant surface comprises one or more inferior positioning grooves having a shape corresponding to and a size larger than an inferior positioning rail, wherein the inferior positioning grooves slidably engage a corresponding inferior positioning rail such that the implant can be slid along the positioning rail and into place in an intervertebral space and such that the corresponding inferior positioning rail can be slidably removed from the intervertebral space along the positioning grooves without disturbing the implant;
   sidewalls separating the superior implant surface and the inferior implant surface, wherein the sidewalls comprise cutouts;
   a central void space for packing bone growth material or bridging bone, wherein the central void space is accessible via the cutouts; and
   wherein when the implant is implanted in the intervertebral space between adjacent vertebrae, the superior implant surface engages a vertebral surface of a superior vertebra and the inferior implant surface engages a vertebral surface of an inferior vertebra.

2. The spinal implant according to claim 1, wherein the spinal implant is an anterior cervical discectomy and fusion (ACDF) implant;

wherein the spinal implant has a height at an anterior wall of about 4 mm to 14 mm;
wherein the spinal implant has a height at a posterior wall of about 4 mm to 98 mm;
wherein the spinal implant has a width from a first side wall to a second wall of about 10 mm to 16 mm; and
wherein the spinal implant has a length from the anterior wall to the posterior wall of about 11 mm to 14 mm.

3. The spinal implant according to claim 2, wherein the one or more superior positioning grooves and the one or more inferior positioning grooves have a length extending from an anterior region of the intervertebral space to a posterior region of the intervertebral space when the implant is implanted in an intervertebral space.

4. The spinal implant according to claim 1, wherein an anterior wall is curved to accommodate a lordotic curvature of the cervical spine, and wherein a posterior wall is about 2 mm to 4 mm shorter than the anterior wall.

5. The spinal implant according to claim 1, wherein the spinal implant is an anterior cervical corpectomy implant;
wherein the spinal implant has a height at an anterior wall of about 14 mm to 100 mm and a width at the anterior wall of about 10 mm to 16 mm;
wherein the spinal implant has a height at a posterior wall of about 4 mm to 100 mm and a width at the posterior wall of about 5 mm to 20 mm; and
wherein the spinal implant has a length from the anterior wall to the posterior wall of about 4 mm to 100 mm.

6. The spinal implant according to claim 5, wherein the sidewalls taper outward from the anterior wall to the posterior wall.

7. The spinal implant according to claim 1, wherein the superior implant surface comprises two superior positioning grooves, and wherein each of the superior positioning grooves receives one of the corresponding superior positioning rails.

8. The spinal implant according to claim 1, wherein the inferior implant surface comprises two inferior positioning grooves, and wherein each of the inferior positioning grooves receives one of the corresponding inferior positioning rails.

9. The spinal implant according claim 1, wherein one or both of the superior implant surface and the inferior implant surface comprise a feature and/or a textured surface that increases a frictional resistance between that surface of the implant and the adjacent vertebrae compared to the same surface in an otherwise same implant except without the features or texture.

10. The spinal implant according claim 1, wherein one or both of the superior implant surface and the inferior implant surface comprise a convex surface.

11. The spinal implant according claim 1, further comprising one or more radiopaque markers.

12. The spinal implant according claim 1, further comprising a central void space, wherein the central void space comprises up to about 90% of a volume of the implant.

13. The cervical spinal implant according to claim 1, wherein the superior positioning grooves have a semi-cylindrical profile, wherein the superior positioning rail is semi-cylindrical, wherein the inferior positioning grooves have a semi-cylindrical profile, and wherein the inferior positioning rail is semi-cylindrical.

14. A thoracolumbar spinal implant comprising:
a superior implant surface, wherein the superior implant surface comprises two superior positioning grooves having a shape corresponding to and a size larger than a superior positioning rail, wherein each of the superior positioning grooves receives one of the corresponding superior positioning rails,
wherein the superior positioning grooves slidably engage a corresponding superior positioning rail such that the implant can be slid along the superior positioning rail and into place in an intervertebral space and such that the corresponding superior positioning rail can be slidably removed from the intervertebral space along the positioning grooves without disturbing the implant;
an inferior implant surface, wherein the inferior implant surface comprises two inferior positioning grooves having a shape corresponding to and a size larger than an inferior positioning rail, wherein each of the inferior positioning grooves receives one of the corresponding inferior positioning rails,
wherein the inferior positioning grooves slidably engage a corresponding inferior positioning rail such that the implant can be slid along the positioning rail and into place in an intervertebral space and such that the corresponding inferior positioning rail can be slidably removed from the intervertebral space along the positioning grooves without disturbing the implant;
sidewalls separating the superior implant surface and the inferior implant surface, wherein the sidewalls comprise cutouts;
a central void space for packing bone growth material or bridging bone, wherein the central void space is accessible via the cutouts; and
a multifunction window in an anterior wall;
wherein when the implant is implanted in the intervertebral space between adjacent vertebrae, the superior implant surface engages a vertebral surface of a superior vertebra and the inferior implant surface engages a vertebral surface of an inferior vertebra;
wherein the spinal implant has a height at the anterior wall of about 4 mm to 25 mm;
wherein the spinal implant has a height at a posterior wall of about 4 mm to 25 mm;
wherein the spinal implant has a width from a first side wall to a second side wall of about 20 mm to 100 mm; and
wherein the implant has a substantially rectangular prism shape.

15. The spinal implant according to claim 14, wherein the superior implant surface and the inferior implant surface are convex.

16. The thoracolumbar spinal implant according to claim 14, wherein the superior positioning grooves have a semi-cylindrical profile, wherein the superior positioning rail is semi-cylindrical, wherein the inferior positioning grooves have a semi-cylindrical profile, and wherein the inferior positioning rail is semi-cylindrical.

17. A lumbar interbody fusion spinal implant comprising:
a superior implant surface, wherein the superior implant surface comprises a superior positioning groove having a semi-cylindrical profile corresponding to a shape of a superior positioning rail and a size larger than the superior positioning rail, wherein the superior positioning groove slidably engages the superior positioning rail such that the implant can be slid along the superior positioning rail and into place in an intervertebral space and such that the superior positioning rail can be slidably removed from the intervertebral space along the superior positioning groove without disturbing the implant;

an inferior implant surface, wherein the inferior implant surface comprises an inferior positioning groove having a semi-cylindrical profile corresponding to a shape of a and a size larger than the inferior positioning rail, wherein the inferior positioning groove slidably engages the inferior positioning rail such that the implant can be slid along the inferior positioning rail and into place in an intervertebral space and such that the inferior positioning rail can be slidably removed from the intervertebral space along the inferior positioning groove without disturbing the implant;

wherein each of the superior and inferior positioning grooves have a length of about 8 mm to about 60 mm and a diameter perpendicular to the length of about 1.5 mm to 2.0 mm, sidewalls separating the superior implant surface and the inferior implant surface, wherein the sidewalls comprise cutouts; and a central void space for packing bone growth material or bridging bone, wherein the central void space is accessible via the cutouts;

wherein when the implant is implanted in the intervertebral space between adjacent vertebrae, the superior implant surface engages a vertebral surface of a superior vertebra and the inferior implant surface engages a vertebral surface of an inferior vertebra;

wherein the spinal implant has a height at an anterior wall of about 4 mm to 20 mm; and wherein the spinal implant has a height at a posterior wall of about 4 mm to 20 mm.

18. The spinal implant according to claim 17, wherein the superior implant surface and the inferior implant surface are convex and wherein the implant has a substantially rectangular prism shape.

19. The spinal implant according to claim 17, wherein the spinal implant is a transforaminal lumbar interbody fusion implant and wherein the implant and positioning grooves are mediolaterally curved.

20. An anterior lumbar interbody fusion implant comprising:
 a first superior positioning groove, a second superior positioning groove, a first inferior positioning groove, and a second inferior positioning groove;
 further comprising a first superior oblique groove, a second superior oblique groove, a first inferior oblique groove, and a second inferior oblique groove;
 wherein the oblique grooves have a larger diameter than the positioning grooves;
 sidewalls separating the superior implant surface and the inferior implant surface, wherein the sidewalls comprise cutouts; and
 a central void space for packing bone growth material or bridging bone, wherein the central void space is accessible via the cutouts;
 wherein when the implant is implanted in the intervertebral space between adjacent vertebrae, the superior implant surface engages a vertebral surface of a superior vertebra and the inferior implant surface engages a vertebral surface of an inferior vertebra;
 wherein the spinal implant has a height at an anterior wall of about 4 mm to 20 mm;
 wherein the spinal implant has a height at a posterior wall of about 4 mm to 20 mm; and
 wherein the spinal implant has a width from a first side wall to a second side wall of about 20 mm to 50 mm.

\* \* \* \* \*